(12) United States Patent
Hwang et al.

(10) Patent No.: US 10,539,463 B2
(45) Date of Patent: Jan. 21, 2020

(54) MOBILE MULTISPECTRAL IMAGING DEVICE, USER TERMINAL FOR ACQUIRING MULTISPECTRAL IMAGE, SPECTRAL IMAGE ANALYSIS SERVER AND METHOD THEREOF

(71) Applicant: DAEGU GYEONGBUK INSTITUTE OF SCIENCE AND TECHNOLOGY, Daegu (KR)

(72) Inventors: Jae Youn Hwang, Daegu (KR); Sewoong Kim, Daegu (KR); Jin Man Park, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 15/559,733

(22) PCT Filed: Apr. 1, 2016

(86) PCT No.: PCT/KR2016/003394
§ 371 (c)(1),
(2) Date: Sep. 19, 2017

(87) PCT Pub. No.: WO2016/159710
PCT Pub. Date: Oct. 6, 2016

(65) Prior Publication Data
US 2018/0100764 A1 Apr. 12, 2018

(30) Foreign Application Priority Data
Apr. 3, 2015 (KR) .................. 10-2015-0047689

(51) Int. Cl.
*G01J 3/28* (2006.01)
*A61B 5/00* (2006.01)
(Continued)

(52) U.S. Cl.
CPC .......... *G01J 3/2823* (2013.01); *A61B 5/0075* (2013.01); *A61B 5/444* (2013.01); *G01J 3/0272* (2013.01);
(Continued)

(58) Field of Classification Search
CPC ...... G01J 3/2823; G01J 3/0272; G01J 3/2803; G01J 3/32; G01J 2003/1213;
(Continued)

(56) References Cited

U.S. PATENT DOCUMENTS

2001/0035957 A1* 11/2001 Clermont .................. G01J 3/02
356/451
2007/0268377 A1* 11/2007 Nagano .................. H04N 9/045
348/222.1
(Continued)

FOREIGN PATENT DOCUMENTS

JP H06-292653 10/1994
KR 2005-0076233 7/2005
(Continued)

OTHER PUBLICATIONS

English Machine Translation of WO2013098512 (Year: 2013).*
International Search Report issued in Application No. PCT/KR2016/003394, dated Jul. 29, 2016.

*Primary Examiner* — Dominic J Bologna
(74) *Attorney, Agent, or Firm* — Norton Rose Fulblright US LLP

(57) ABSTRACT

Provided are a mobile multispectral imaging device, a user terminal for acquiring a multispectral image, a spectral image analysis server, and a method thereof. A mobile multispectral imaging device, according to an embodiment of the present invention, is for taking spectral images for respective wavelengths by using a photographing unit of a user terminal. The mobile multispectral imaging device comprises: an optical system, positioned in a place corre-
(Continued)

sponding to the photographing unit of the user terminal, which irradiates light to an object to be photographed, collects the light reflected from the object to be photographed, and transfers the light to the photographing unit; and a filter wheel, which is provided with a plurality of optical filters spaced apart from one another and positions one of the plurality of optical filters in an optical path according to rotation, wherein the plurality of optical filters filter an irradiated light in a specific wavelength.

6 Claims, 10 Drawing Sheets

(51) Int. Cl.
*G01J 3/02* (2006.01)
*G06T 7/00* (2017.01)
*G01J 3/32* (2006.01)
*G01J 3/12* (2006.01)

(52) U.S. Cl.
CPC ..... *G06T 7/0012* (2013.01); *G01J 2003/2826* (2013.01)

(58) Field of Classification Search
CPC ....... G01J 2003/1217; G01J 2003/1221; G01J 2003/2826; A61B 5/0013; A61B 5/0075; A61B 5/0077; A61B 5/444; G06T 7/0012
See application file for complete search history.

(56) References Cited

U.S. PATENT DOCUMENTS

| | | | | |
|---|---|---|---|---|
| 2013/0293702 | A1* | 11/2013 | Xin | ........................ G01J 3/0208 348/135 |
| 2013/0300919 | A1* | 11/2013 | Fletcher | .................. H04M 1/21 348/360 |
| 2014/0323873 | A1 | 10/2014 | Cummins et al. | ............. 600/473 |
| 2016/0098614 | A1* | 4/2016 | Yamanashi | .......... G06K 9/4661 348/135 |

FOREIGN PATENT DOCUMENTS

| | | | |
|---|---|---|---|
| KR | 10-1425203 | 8/2014 | |
| KR | 2014-0112046 | 9/2014 | |
| WO | WO 2013/096766 | 6/2013 | |
| WO | WO-2013098512 A1 * | 7/2013 | ........... A61B 5/7264 |

* cited by examiner

MOBILE MULTISPECTRAL IMAGING DEVICE, USER TERMINAL FOR ACQUIRING MULTISPECTRAL IMAGE, SPECTRAL IMAGE ANALYSIS SERVER AND METHOD THEREOF

CROSS REFERENCE TO RELATED APPLICATIONS

This application is a national phase application under 35 U.S.C. § 371 of International Application No. PCT/KR2016/003394, filed Apr. 1, 2016, which claims priority to Korean Application No. 10-2015-0047689, filed Apr. 3, 2015. The contents of the referenced applications are incorporated in the present application by reference.

FIELD OF THE DISCLOSURE

The present invention relates to a mobile multispectral imaging device, a user mobile device connection, and an image analysis method for skin healthcare, and more particularly, to a mobile multispectral imaging device, a user terminal for acquiring a multispectral image, a spectral image analysis server, and a method thereof, which can diagnose and manage skin by using spectral images of multiple wavelengths.

DESCRIPTION OF RELATED ART

Generally, spectral imaging and spectral image analysis techniques are useful used in a diagnosis of various diseases and a bio-application. Particularly, the spectral imaging technique has been proven useful in diagnosis of skin cancer, and commercialization thereof is in progress.

However, an existing spectral imaging technique consists of devices specialized for detailed functions, such as a light source for acquiring an image, a device for spectral filtering of the light source, a camera device for capturing a filtered image, a device for analyzing the captured image, and the like. Hence, these devices must be individually purchased and connected to a computer to receive or analyze acquired images, and thereby additional conditions such as the development of dedicated software and an addition of a device to be connected are required.

In addition, devices which provide detailed functions are intended for medical professionals, such as doctors, and have a problem in that they are not suitable for use in a general household because there are many limitations in using them as home medical devices.

SUMMARY OF THE INVENTION

In order to solve the foregoing problems of the existing technique, an objective of one embodiment of the present invention is to provide a mobile multispectral imaging device, a user terminal for acquiring a multispectral image, a spectral image analysis server, and a method thereof, which facilitate capturing a spectral image for skin healthcare by using a user terminal, such as a smartphone or a tablet computer.

In addition, another objective of one embodiment of the present invention is to provide a mobile multispectral imaging device, a user terminal for acquiring a multispectral image, a spectral image analysis server, and a method thereof which allow a layman to easily provide skin healthcare service to a user.

One aspect of the present invention provides a mobile multispectral imaging device which is a mobile spectral imaging device for capturing a wavelength-specific spectral image by using a photographing unit of a user terminal, the mobile multispectral imaging device including: an optical system which is disposed at a position corresponding to the photographing unit of the user terminal and is configured to emit light toward an object to be photographed, collect light reflected from the object to be photographed, and transmit the collected light to the photographing unit; and a filter wheel which includes a plurality of optical filters spaced apart from each other and places one of the plurality of optical filters in an optical path according to rotation thereof, wherein each of the optical filters filters the emitted light into a specific wavelength band.

The mobile multispectral imaging device may further include a driving unit configured to drive the filter wheel to place one selected filter wheel in the optical path in response to a photographing request of the user terminal.

The driving unit may continuously rotate the filter wheel on the basis of a photographing speed of the photographing unit.

The mobile multispectral imaging device may further include a communication unit configured to receive a photographing request or a control command from the user terminal.

The optical system may include a polarimeter in an optical path of the photographing unit.

The polarimeter may include at least one of a horizontal polarimeter provided in an optical path of the optical filter and configured to provide the light to the object to be photographed and a vertical polarimeter configured to collect the light reflected from the object to be photographed and transmit the collected light to the photographing unit.

The mobile multispectral imaging device may further include a main body on which the user terminal is mounted and a cover unit including a through-hole at a position corresponding to the optical system.

The filter wheel may include the plurality of optical filters disposed at equal intervals around an outer circumference thereof and include a wheel shaft coupled to the driving unit.

The horizontal polarimeter and a magnifying glass may be disposed in the optical system, and the optical system may further include an optical system fixing portion having a groove portion formed below the horizontal polarimeter to allow the filter wheel to rotate.

The optical system may further include a light source configured to emit light toward the object to be photographed.

The optical system may further include a light source for skin treatment which treats a skin lesion.

Another aspect of the present invention provides a user terminal for acquiring a multispectral image by controlling a mobile multispectral imaging device including a plurality of optical filters which each filter light into a specific wavelength band, the user terminal including: a photographing unit; and a controller configured to control the photographing unit to capture spectral images corresponding to each specific wavelength band by adjusting positions of the plurality of optical filters, wherein the spectral image corresponding to a target wavelength band is captured and acquired by selectively driving an optical filter corresponding to the target wavelength band among the plurality of optical filters.

The user terminal may further include a light source configured to transmit light toward the photographing unit, and a storage unit configured to store an image acquired by the photographing unit.

The user terminal may further include a user setting unit configured to receive a photographing setting of the photographing unit, a setting of the mobile multispectral imaging device, and a setting of a target image among the spectral images corresponding to each of the wavelength bands.

The user terminal may further include a communication unit configured to communicate with the mobile multispectral imaging device to transmit a photographing request or a control command of the controller.

The controller may include a zero-point adjustment module configured to adjust a position of the optical filter corresponding to the target wavelength band in order to adjust a focal point onto an object to be photographed, an image capturing module configured to acquire spectral images in wavelength bands corresponding to each of the optical filters by continuously adjusting the positions of the plurality of optical filters on the basis of a photographing speed of the photographing unit, and an image transmission module configured to transmit a spectral image selected by a user to a spectral image analysis server.

Still another aspect of the present invention provides a spectral image analysis server which receives and analyzes a wavelength-specific spectral image captured using a plurality of optical filters of a mobile multispectral imaging device on which a user terminal is mounted, the spectral image analysis server including: an analysis information storage unit configured to store a type and characteristic of a skin lesion to be analyzed and a reference value of each wavelength band for each skin lesion; and a diagnosis unit configured to diagnose a skin condition by comparing and analyzing the received wavelength-specific spectral image with a reference value of each wavelength band which corresponds to each of the skin lesions.

The spectral image analysis server may further include: a statistics processor configured to quantitatively analyze changes of a specific skin lesion diagnosed by the diagnosis unit and quantitatively analyze a comparison thereof with normal skin; and an information providing unit configured to provide relevant information including a treatment method for a skin lesion diagnosed as the skin condition, a method of preventing aggravation, or a hospital available for treatment.

The diagnosis unit may extract a pixel value at a position of a lesion in each of spectral image, check a reference value corresponding to the lesion, and generate a spectral spectrum by classifying the extracted pixel value and the reference value by wavelength.

The spectral image analysis server may further include: a user information storage unit configured to store user information that corresponds to the user terminal and an image transmitted from the user terminal; and a provision information storage unit configured to store provision information including a treatment method for a skin lesion, a method for preventing aggravation, or a hospital available for treatment.

Yet another aspect of the present invention provides a method of acquiring a spectral image which corresponds to a wavelength band, the method including: mounting a mobile spectral imaging device provided with a plurality of optical filters on a user terminal including a photographing unit; selectively placing an optical filter that corresponds to a target wavelength band among the plurality of the optical filters in an optical path corresponding to the photographing unit; and capturing a spectral image that corresponds to the wavelength band, wherein the plurality of optical filters are rotated to selectively place the optical filter that corresponds to the target wavelength band in the optical path.

The capturing of the spectral image may include continuously rotating the plurality of optical filters on the basis of a photographing speed of the photographing unit so that one selected optical filter is placed in the optical path in response to a photographing request of the user terminal.

The optical filter that corresponds to the target wavelength band may be selectively placed in the optical path by rotating a filter wheel in which the plurality of optical filters are spaced apart from each other at regular intervals.

Still another aspect of the present invention provides a method of analyzing a spectral image which corresponds to a wavelength band, the method including: acquiring a wavelength-specific spectral image from a user terminal, which includes a photographing unit, and a mobile spectral imaging device, which includes a plurality of optical filters, by selecting an optical filter that corresponds to a specific wavelength band among the plurality of optical filters by rotating the plurality of optical filters; and diagnosing a skin condition by comparing and analyzing the spectral image in each wavelength band with a reference value for each of the wavelength bands which is stored in advance for each skin lesion.

The diagnosing of the skin condition may include extracting a pixel value at a position of a lesion in the image, checking a reference value that corresponds to the lesion, and generating a spectral spectrum by classifying the extracted pixel value and the reference value by the wavelength.

The method may further include providing relevant information including a treatment method for the diagnosed skin lesion, a method for preventing aggravation, or a hospital available for treatment.

According to one embodiment of the present invention, it is possible to easily diagnose a skin disease and conveniently and regularly manage skin at home by using a user terminal, such as a smartphone or a tablet computer.

In addition, according to one embodiment of the present invention, it is possible to provide continuous skin care mentoring by build a database including a variety of information, such as a treatment method and post-treatment care of a skin-related disease, kinds of skin-related diseases, and a treatment method for a current skin condition.

Moreover, it is possible to diagnose a skin disease, which is increasing due to environmental or genetic factors, at an early stage, thereby alleviating social and economic costs associated with the skin disease.

DETAILED DESCRIPTION OF THE INVENTION

Figure 1A:
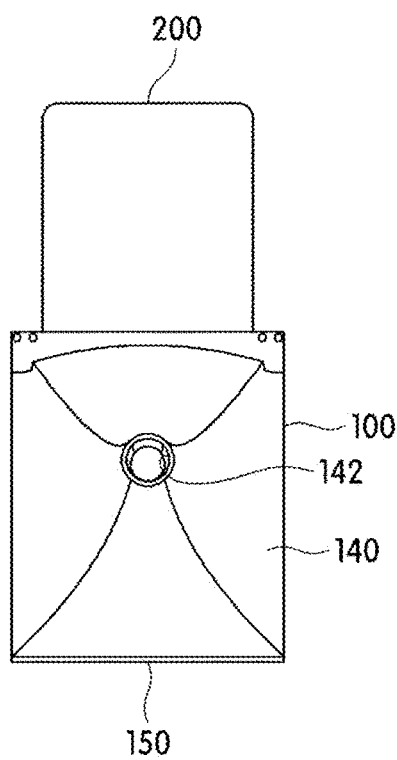
FIGS. 1A and 1B are a front view and a rear view of a mobile multispectral imaging device with a user terminal mounted thereto according to one embodiment of the present invention.

The present invention will be described more fully hereinafter with reference to the accompanying drawings, in which exemplary embodiments of the invention are shown, to be easily performed by those skilled in the art. However, the invention may be embodied in many different forms and is not to be construed as being limited to the embodiments set forth herein. Also, irrelevant details have been omitted from the drawings for increased clarity and conciseness, and similar parts are indicated by similar reference numerals throughout the detailed description.

Figure 1B:
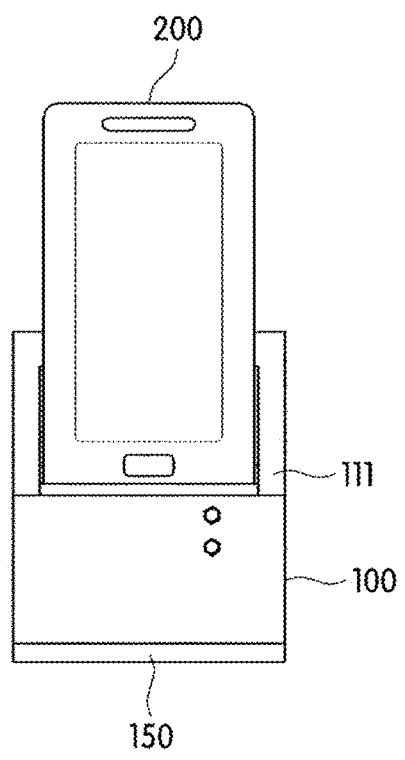
Figure 2:
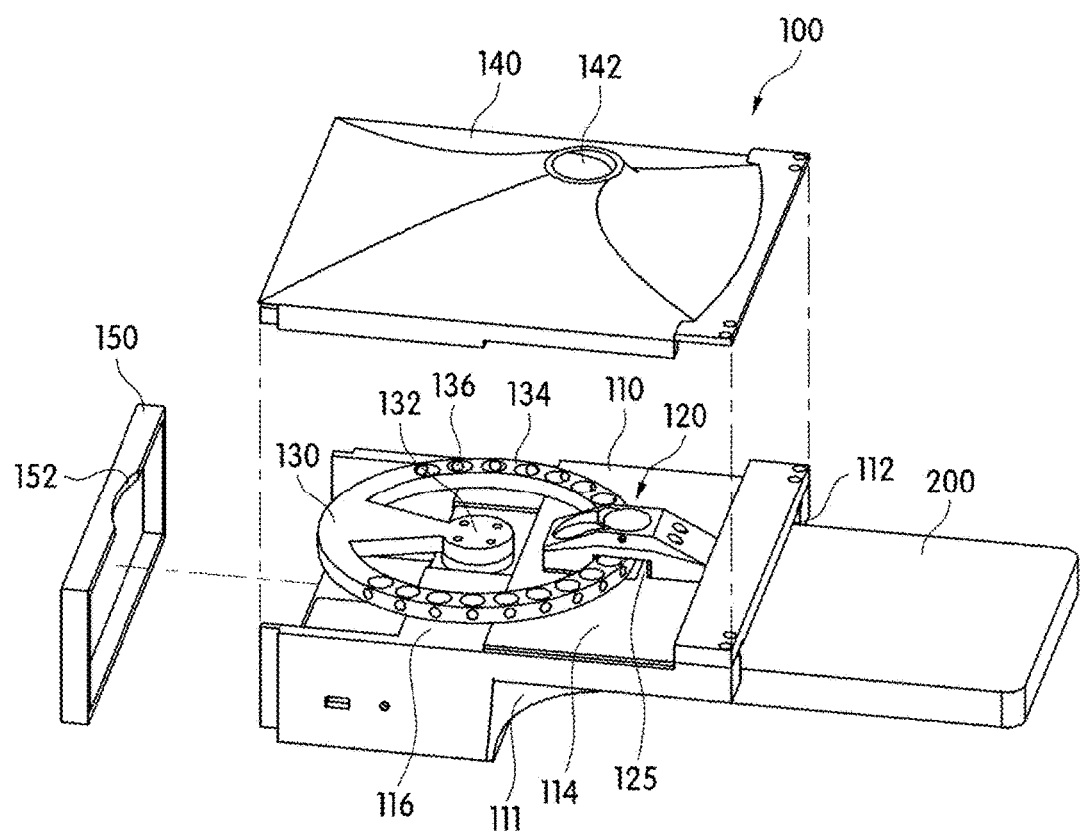
FIGS. 2 and 3 are exploded perspective views of a mobile multispectral imaging device according to one embodiment of the present invention.
Figure 3:
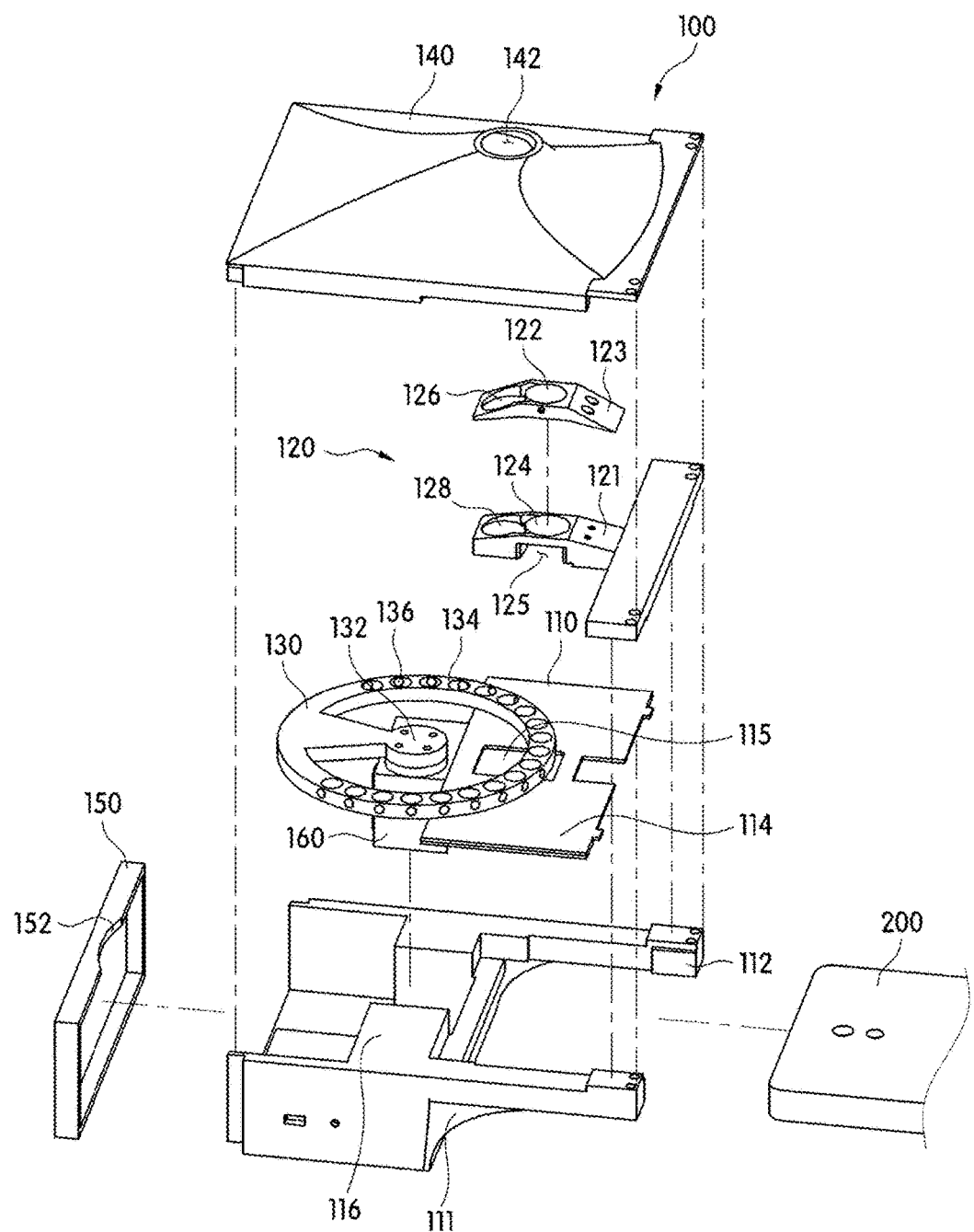
Figure 4:
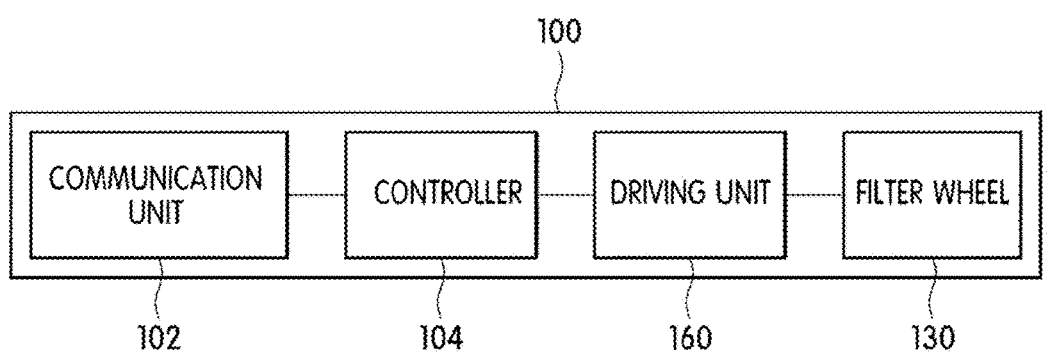
FIG. 4 is a block diagram illustrating a detailed configuration of a mobile multispectral imaging device according to one embodiment of the present invention.

FIGS. 1A and 1B are a front view and a rear view of a mobile multispectral imaging device with a user terminal mounted thereto according to one embodiment of the present invention, FIGS. 2 and 3 are exploded perspective views of a mobile multispectral imaging device according to one embodiment of the present invention, and FIG. 4 is a block diagram illustrating a detailed configuration of a mobile multispectral imaging device according to one embodiment of the present invention. Hereinafter, the mobile multispectral imaging device according to the embodiment of the present invention will be described in detail with reference to the drawings.

Referring to FIGS. 1 to 3, a mobile spectral imaging device 100 according to one embodiment of the present invention includes a main body 110, an optical system 120, a filter wheel 130, a cover unit 140, and a side cover 150.

The mobile spectral imaging device 100 may be equipped with a user terminal 200, such as a smartphone or a tablet computer, having a photographing function for acquiring a multispectral image, and may capture wavelength-specific spectral images of the skin of an object to be photographed by using the photographing function of the user terminal 200, such as a light source and a photographing unit.

The user terminal 200 may be mounted on the main body 110, and the optical system 120, the filter wheel 130, and a driving unit 160 may be disposed at the main body 110. A mounting groove 112 for mounting the user terminal 200 may be provided on one side of the main body 110, and a terminal mounting portion 111, on which the user terminal 200 is mounted, may be formed on a rear surface, as shown in FIGS. 1A and 1B.

An optical system mounting portion 114 is formed close to the mounting groove 112, and as will be described below, the optical system 120 is disposed thereon. As shown in FIG. 3, a through-hole 115 may be formed at the center of the optical system mounting portion 114 such that the light source and the photographing unit of the user terminal 200 communicate with the optical system 120 when the user terminal 200 is mounted on the main body 110. That is, through the through-hole 115, light emitted from the light source may be directed toward the skin of the object to be photographed and light reflected from the skin of the object to be photographed may be collected at the user terminal 200.

In this case, the light source is described as the light source of the user terminal 200, but is not limited thereto, and the light source may be individually provided in the optical system 120. Hereinafter, the light source of the user terminal may be construed as being separately provided in the optical system.

A motor mounting portion 116 may be formed close to the optical system mounting portion 114, and the driving unit 160 may be disposed at the motor mounting portion 116. In this case, the motor mounting portion 116 may have a groove portion to accommodate the driving unit 160.

The optical system 120 is disposed at a position corresponding to the photographing unit of the user terminal 200, and, for example, may be disposed at the optical system mounting portion 114. The optical system 120 may include an optical system fixing portion 121 and an optical system cover 123. In this case, the optical system fixing portion 121 may extend from the mounting groove 112 to a center portion to be positioned corresponding to a position of the light source and the photographing unit of the user terminal 200.

The optical system 120 may direct the light emitted from the light source of the user terminal 200 or a light source of the optical system 120 toward the skin of the object to be photographed, and may collect the light reflected from the skin of the object to be photographed and transmit the collected light to the photographing unit of the user terminal 200. In this case, the optical system 120 may include a polarimeter in an optical path of the photographing unit of the user terminal 200.

A horizontal polarimeter 124 and magnifying glass 128 may be disposed above the optical system fixing portion 121, and a groove portion 125 may be formed below the horizontal polarimeter 124. The groove portion 125 may allow the filter wheel 130 to rotate.

The horizontal polarimeter 124 may be provided in an optical path of an optical filter 136 and transmit the light to the object to be photographed. For example, the horizontal polarimeter 124 may be optically coupled to one optical filter selected from the light source of the user terminal 200 and the optical filter 136 of the filter wheel 130. The horizontal polarimeter 124 may horizontally polarize the light transmitted from the light source of the user terminal 200 through the optical filter 136 and transmit the polarized light to a planoconcave lens 122.

The magnifying glass 128 may be optically coupled to a vertical polarimeter 126, collect the light reflected from the skin of the object to be photographed through the vertical polarimeter 126, and transmit the collected light to the photographing unit of the user terminal 200.

The planoconcave lens 122 and the vertical polarimeter 126 may be disposed at the optical system cover 123. In this case, the planoconcave lens 122 may be located collinearly above the horizontal polarimeter 124, and the vertical polarimeter 126 may be located collinearly above the magnifying glass 128.

The planoconcave lens 122 may be optically coupled to the vertical polarimeter 126 and divert the light passing through the optical filter 136 and the horizontal polarimeter 124 from the light source of the user terminal 200 toward the skin of the object to be photographed.

The vertical polarimeter 126 may collect the light reflected from the skin to be photographed and transmit the collected light to the photographing unit of the user terminal 200. For example, the vertical polarimeter 126 may collect the light reflected from the skin of the object to be photographed by being emitted through the planoconcave lens 122. In this case, the vertical polarimeter 126 may polarize the collected light vertically and transmit the polarized light to the magnifying glass 128.

Although the horizontal polarimeter 124 is described as being located in an optical path which is collinear with the light source of the user terminal 200 and the vertical polarimeter 126 is described as being located in an optical path which is collinear with a photographing unit 210 in the present embodiment, the present embodiment is not limited thereto, and different polarimeters may be disposed in the optical paths of the light source and the photographing unit of the user terminal 200.

In this case, the polarimeter may have an orthogonal polarization function. That is, the vertical polarimeter 126 may be located in an optical path which is collinear with the light source of the user terminal, and the horizontal polarimeter 124 may be positioned in the optical path which is collinear with the photographing unit of the user terminal 200.

Alternatively, the spectral imaging device 100 according to one embodiment of the present invention may include either the horizontal polarimeter 124 or the vertical polarimeter 126. In this case, the polarimeter included in the spectral imaging device 100 may be positioned in either the optical path of the photographing unit of the user terminal 200 or the optical path of the light source.

The filter wheel 130 may include a plurality of optical filters 136 which are spaced apart from each other and which each filter the light emitted from the light source into a specific wavelength band, and one of the plurality of optical filters 136 may be placed in an optical path in accordance with a rotation of the filter wheel 130. The filter wheel 130 is rotatable such that one selected optical filter 136 is disposed in line with the light source of the user terminal 200 in response to a photographing request of the user terminal 200.

As shown in FIG. 2, the filter wheel 130 may have the plurality of optical filters 136 disposed at equal intervals around an outer circumference thereof, and may have a wheel shaft 132 coupled to the driving unit 160. The filter wheel 130 may rotate through the groove portion 125 of the optical system fixing portion 121. In this case, a rotation direction of the filter wheel 130 may be reversed with respect to the optical filter 136 disposed at the leftmost position and the optical filter 136 disposed at the rightmost position.

The plurality of optical filters 136 may be interposed between the light source of the user terminal 200 and the horizontal polarimeter 124 and filter the light emitted from the light source of the user terminal 200 into a plurality of predetermined wavelength bands. For example, the plurality of optical filters 136 may pass wavelength bands of 400 nm to 700 nm, and each of the filters may have a bandwidth of 35 nm or less. The optical filters 136 may be optically coupled to the horizontal polarimeter 124 and transmit the light filtered into the wavelength of each bandwidth to the horizontal polarimeter 124.

Although it is described that light of a specific wavelength is provided while one light source is used by rotating the filter wheel having the plurality of optical filters in the present embodiment, configurations of the light source and the optical filters are not limited thereto.

For example, when the light source is separately provided inside the optical system, a plurality of light sources may be provided. In this case, one light source and one optical filter may be paired, and pairs of the light source and the optical filter may be provided at the filter wheel at equal intervals. In this case, a light source which corresponds to an optical filter of a desired wavelength band may be turned on among the plurality of light sources and the remaining light sources may be turned off so that light of a specific wavelength may be provided. As such, it is possible to provide the light of the specific wavelength by only controlling ON/OFF of the light source, instead of selecting an optical filter by using the driving unit, such as a motor, to rotate the filter wheel.

The cover unit 140 may cover an upper part of the main body 110 and have a through-hole 142 at a position corresponding to the optical system 120. That is, through the through-hole 142, the light which is emitted from the light source of the user terminal 200 and transmitted through the optical system 120 may be directed toward the skin of the object to be photographed and the light reflected from the skin may be provided to the photographing unit of the user terminal 200 through the optical system 120.

The side cover 150 covers a side surface opposite to the mounting groove 112 and has a function of coupling the main body 110 to the cover unit 140. A curved concave portion 152 corresponding to a shape of the filter wheel 130 may be formed on one side of the side cover 150 so that the rotation of the filter wheel 130 is not hindered.

The driving unit 160 drives the filter wheel 130 to place one selected optical filter 136 in an optical path in response to the photographing request of the user terminal 200. For example, the driving unit 160 may rotate the filter wheel 130 to position the selected optical filter 136 in line with the light source of the user terminal 200. In this case, the driving unit 160 may continuously rotate the filter wheel 130 on the basis of a photographing speed of the photographing unit of the user terminal 200. For example, the driving unit 160 may be configured with a driving motor.

As shown in FIG. 4, the mobile spectral imaging device 100 further includes a communication unit 102 and a controller 104.

The communication unit 102 may receive the photographing request or a control command from the user terminal 200. The communication unit 102 may perform short-range communication, such as Bluetooth, but is not limited thereto, and the communication unit 102 may employ any scheme that allows communication with the user terminal 200.

The controller 104 may control the filter wheel 130 having the plurality of optical filters 136 to continuously rotate in response to a request of the user terminal 200.

Although it is described that light corresponding to a wavelength for treating a skin lesion is output in the present embodiment, a light source for treating the skin lesion may be separately provided. For example, a light-emitting diode (LED) which outputs light in the 650 nm band may be provided in the main body 110. Alternatively, the optical filter 136 having a pass band of 650 nm may be provided and the light source of the user terminal 200 or a light source of the optical system may be utilized as a light source for skin treatment by using the optical filter 136.

Figure 5A:
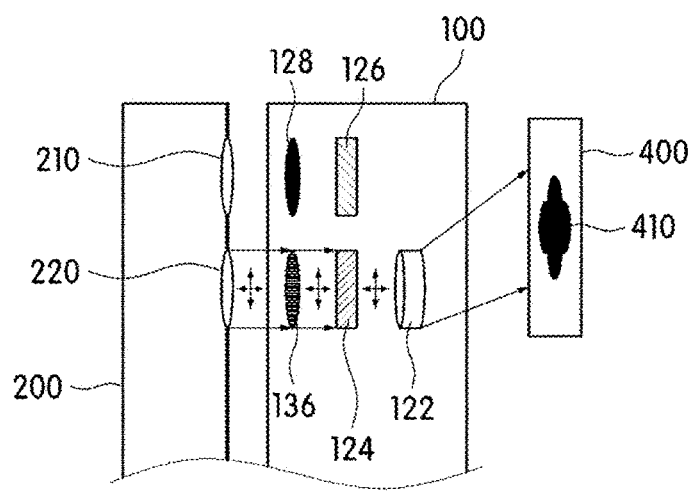
FIGS. 5A and 5B are diagrams for describing a light emitting operation and a photographing operation of an optical system of a mobile multispectral imaging device according to one embodiment of the present invention.
Figure 5B:
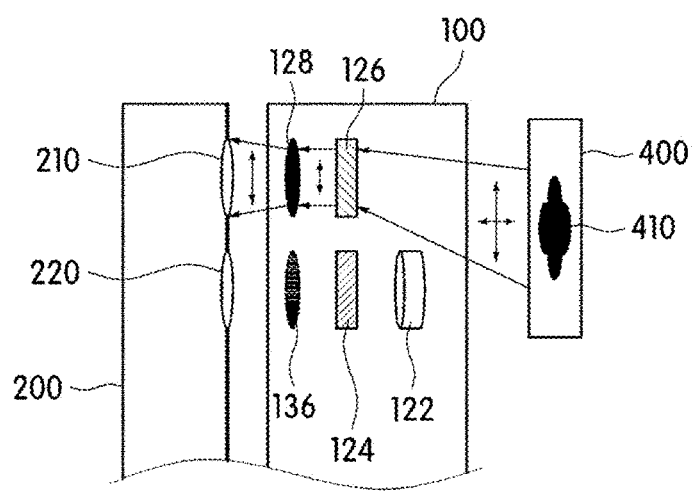

Hereinafter, operations of the mobile spectral imaging device 100 according to an embodiment of the present invention will be described in detail with reference to FIGS. 5A and 5B. FIGS. 5A and 5B are diagrams for describing a light emitting operation and a photographing operation of an optical system of a mobile multispectral imaging device according to one embodiment of the present invention.

As shown in FIG. 5A, first, light output through a light source 220 of the user terminal 200 is filtered by the optical filter 136 into a specific band, polarized horizontally by the horizontal polarimeter 124, and then emitted toward skin 400 to be photographed. In this case, the skin 400 to be photographed may include a skin disease area or a lesion 410.

Then, as shown in FIG. 5B, light reflected from the skin 400 to be photographed may be polarized vertically by the vertical polarimeter 126 and transmitted to the photographing unit 210 of the user terminal 200 through the magnifying glass 128.

The operations shown in FIGS. 5A and 5B may be repeatedly performed for the whole of the plurality of optical filters 136 or for bands associated with a user's setting.

Referring back to FIGS. 1A and 1B, the user terminal 200 may be a mobile communication terminal, such as a smartphone, or a portable personal terminal, such as a tablet computer, with a photographing function.

Figure 6:
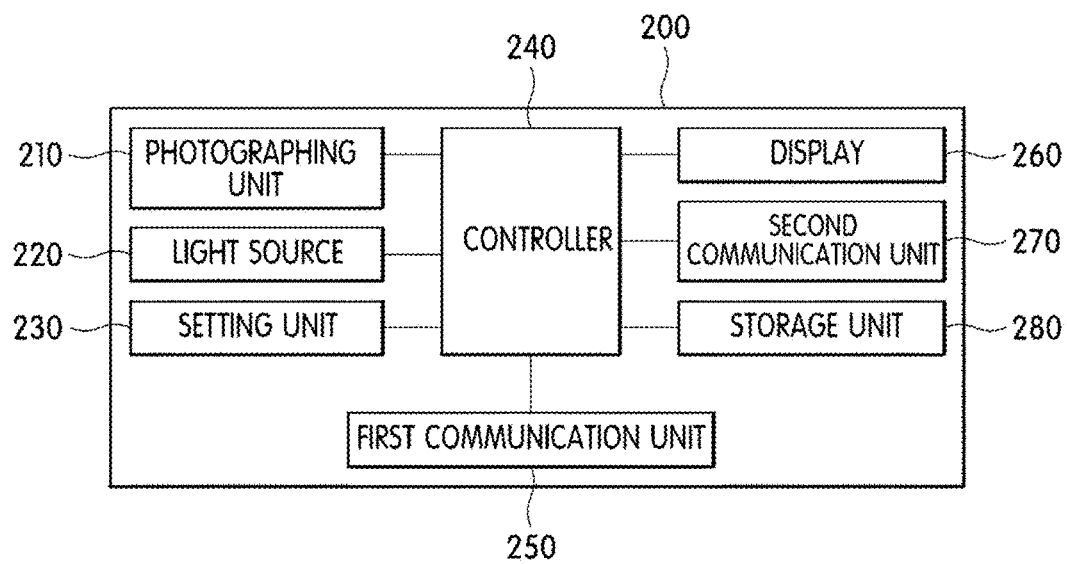
FIG. 6 is a block diagram illustrating a detailed configuration of a user terminal for acquiring a multispectral image according to one embodiment of the present invention.
Figure 7:
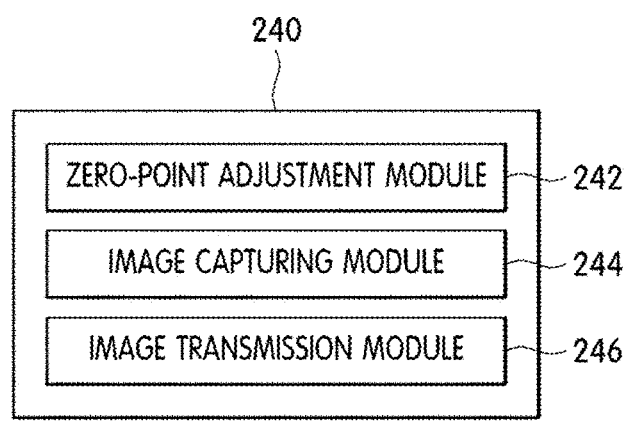
FIG. 7 is a block diagram illustrating a detailed configuration of a controller of FIG. 6.

Hereinafter, the user terminal for acquiring a multispectral image according to one embodiment of the present invention will be described in detail with reference to FIGS. 6 and 7. FIG. 6 is a block diagram illustrating a detailed configuration of the user terminal for acquiring a multispectral image according to one embodiment of the present invention, and FIG. 7 is a block diagram illustrating a detailed configuration of a controller of FIG. 6.

The user terminal 200 may capture and acquire a spectral image that corresponds to a target wavelength band by selectively driving an optical filter that corresponds to the target wavelength band among the plurality of optical filters 136, and the user terminal 200 may include the photographing unit 210, the light source 220, a setting unit 230, a controller 240, a first communication unit 250, a display 260, a second communication unit 270, and a storage unit 280.

The photographing unit 210 is a device capable of capturing an image, and may be, for example, a charge-coupled device (CCD) camera.

The light source 220 may transmit light to the photographing unit 210 and, for example, may emit a flash of light while photographing.

The setting unit 230 may perform photographing setting of the photographing unit 210 using the light source 220, setting of the mobile spectral imaging device 100, and selection of an image to be analyzed among captured and stored images. For example, the setting unit 230 is an input device of the user terminal 200, and may be a touchpad or a keypad.

The controller 240 may control the photographing unit 210 to capture a multispectral image that corresponds to a specific wavelength band by adjusting positions of the plurality of optical filters 136, and may control selection of an image to be transmitted and transmission of the image. In this case, the controller 240 may include a zero-point adjustment module 242, an image capturing module 244, and an image transmission module 246.

The zero-point adjustment module 242 may adjust a position of the optical filter 136 corresponding to the target wavelength band in order to adjust a focal point on the object to be photographed. The zero-point adjustment module 242 may perform pairing with the mobile spectral imaging device 100, adjust a focal point between the skin to be photographed and the optical system 120, and adjust an initial photographing position of the filter wheel 130. In this case, the zero-point adjustment module 242 may perform pairing with the mobile spectral imaging device 100 through Bluetooth communication of the communication unit 102.

The image capturing module 244 may allow for acquiring spectral images in wavelength bands which correspond to each of the optical filters 136 by continuously adjusting the positions of the optical filters 136 on the basis of a photographing speed of the photographing unit 210. That is, the image capturing module 244 may control photographing while rotating the filter wheel 130 continuously so that each of the plurality of optical filters 136 can be positioned in line with the light source 220 according to the photographing setting of the setting unit 230. In this case, the image capturing module 244 may control the rotation of the filter wheel 130 on the basis of the photographing speed of the photographing unit 210.

For example, because a spectral image consists of a plurality of wavelength-specific images, target skin is continuously photographed, and in this case, the image capturing module 244 may control the filter wheel 130 to rotate continuously according to the continuous photographing speed of the photographing unit 210, such as a camera.

In addition, the image capturing module 244 may store the captured images in the storage unit 280. The image capturing module 244 may provide a wavelength-specific selection screen for a user to select a specific wavelength for photographing. With this function, when re-photographing is performed for a specific wavelength at a time of continuous photographing using the plurality of optical filters 136, it is possible to capture an image for a selective wavelength.

The image transmission module 246 may transmit a spectral image selected by the user from stored images to a spectral image analysis server 300. For example, the image transmission module 246 may output acquired images through the display 260 and provide an image selection screen for the user to select an image. In this case, when the user selects all or some of the images, the image transmission module 246 may transmit only the images selected in the display 260 to the spectral image analysis server 300.

Although the mobile spectral imaging device 100 is described as not including a light source for skin lesion treatment in the present embodiment, the mobile spectral imaging device 100 may include the light source for skin lesion treatment or an optical filter 136 in a band that corresponds to the light source. In this case, the controller 240 may control light emitted from a light source to be directed toward skin to be treated, wherein the light source corresponds to a wavelength for treating a skin lesion at a location analyzed by the spectral image analysis server 300.

For example, the controller 240 may control light emitted from a light source for skin care, which is included in the mobile spectral imaging device 100, to be directed toward the skin to be treated. Alternatively, the controller 240 may direct the light emitted from the light source 220 toward the skin to be treated by using an optical filter 136 that corresponds to a wavelength for treatment among the plurality of optical filters 136.

Referring back to FIG. 6, the first communication unit 250 may communicate with the mobile spectral imaging device 100 and transmit a photographing request or a control command of the controller 240 thereto. For example, the communication unit 250 may perform short-range communication, such as Bluetooth communication, but is not limited thereto, and the communication unit 250 may employ any scheme that allows communication with the mobile spectral imaging device 100.

The display 260 may output a spectral spectrum or analysis result received from the spectral image analysis server 300 according to the user's selection. In addition, the display 260 may output a wavelength-specific image obtained by the photographing unit 210. Alternatively, when the spectral image analysis server 300 predicts and diagnoses a disease of the photographed skin, the spectral image analysis server 300 may output the result along with the spectral spectrum.

The second communication unit 270 may communicate with the spectral image analysis server 300. The second communication unit 270 may communicate with the spectral image analysis server 300 through, for example, a wireless communication network or a WiFi network. In this case, the second communication unit 270 may transmit an image selected by the user among the captured images to the spectral image analysis server 300 and receive an analysis result from the spectral image analysis server 300.

The storage unit 280 may store images acquired from the photographing unit 210 through the mobile spectral imaging device 100.

Hereinafter, a spectral image analysis system according to an embodiment of the present invention will be described in detail with reference to FIGS. 8 to 12.

Figure 8:
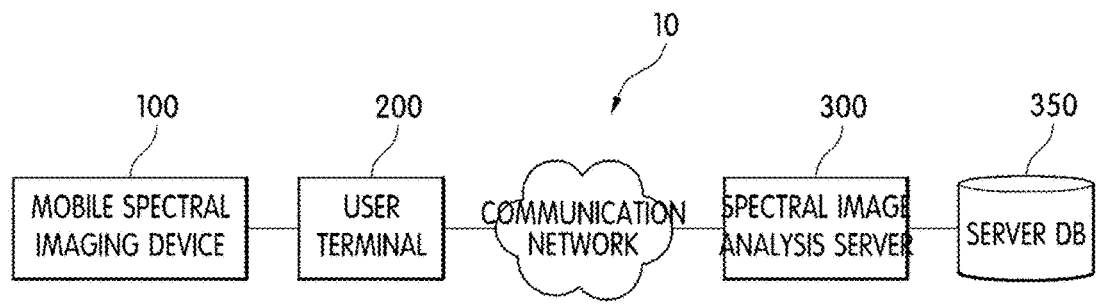
FIG. 8 is a configuration diagram schematically illustrating a spectral image analysis system according to one embodiment of the present invention.
Figure 9:
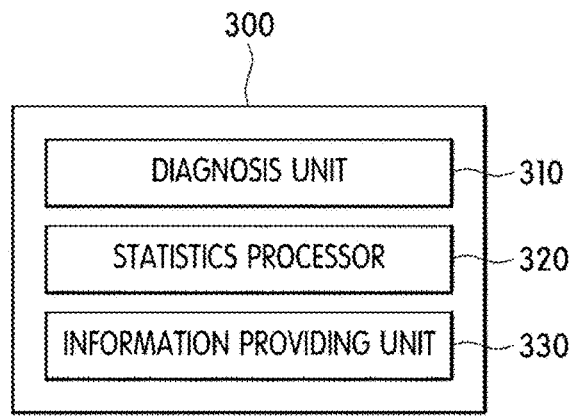
FIG. 9 is a block diagram illustrating a detailed configuration of a spectral image analysis server according to one embodiment of the present invention.
Figure 10:
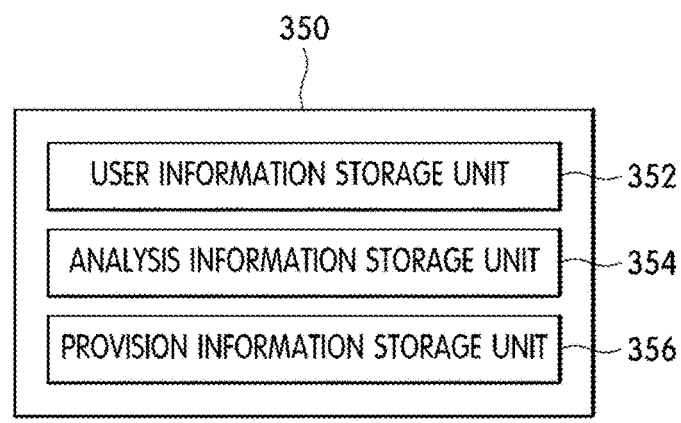
FIG. 10 is a block diagram illustrating a detailed configuration of a server database (DB) of a spectral image analysis server according to one embodiment of the present invention.
Figure 11:
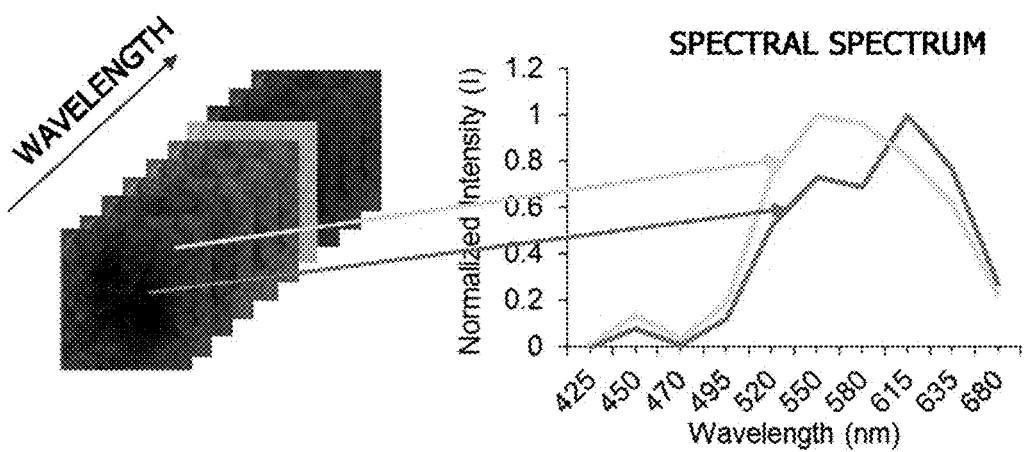
FIG. 11 is a diagram for describing an example of a spectral image analysis or a diagnosis method according to one embodiment of the present invention.
Figure 12:
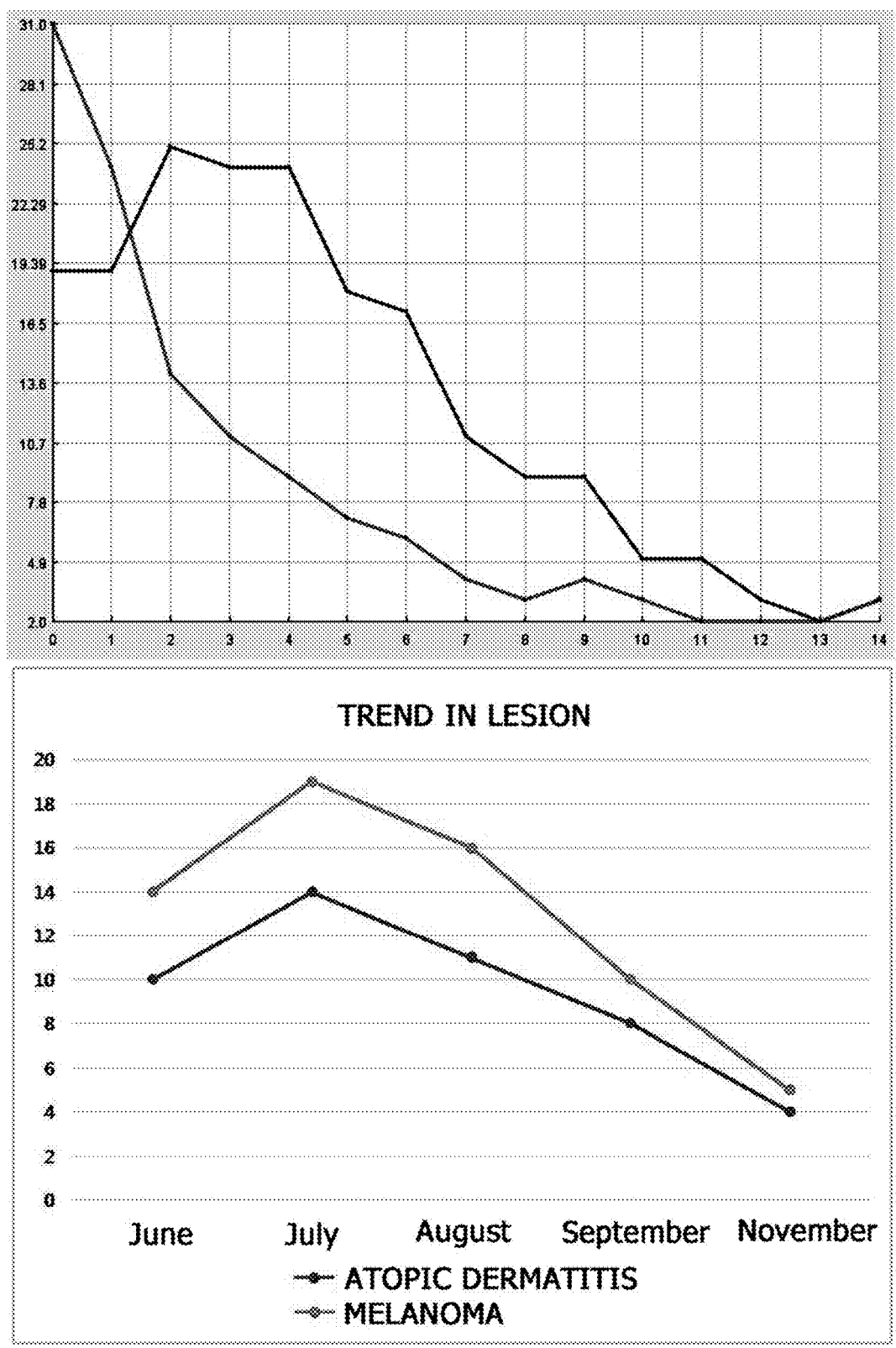
FIG. 12 illustrates graphs for describing another example of a spectral image analysis or diagnosis method according to one embodiment of the present invention.

FIG. 8 is a configuration diagram schematically illustrating a spectral image analysis system according to one embodiment of the present invention, FIG. 9 is a block diagram illustrating a detailed configuration of a spectral image analysis server according to one embodiment of the present invention, FIG. 10 is a block diagram illustrating a detailed configuration of a server database (DB) of a spectral image analysis server according to one embodiment of the present invention, FIG. 11 is a diagram for describing an example of a spectral image analysis or a diagnosis method according to one embodiment of the present invention, and FIG. 12 illustrates graphs for describing another example of a spectral image analysis or diagnosis method according to one embodiment of the present invention.

A spectral image analysis system 10 includes the mobile spectral imaging device 100, the user terminal 200, the spectral image analysis server 300, and a server DB 350. In this case, the mobile spectral imaging device 100 and the user terminal 200 are the same as those described with reference to FIGS. 1 to 7, and thus detailed descriptions thereof will be omitted.

The spectral image analysis server 300 receives and analyzes wavelength-specific spectral images captured using the plurality of optical filters 136 of the mobile multispectral imaging device 100 on which the user terminal 200 is mounted, and includes a diagnosis unit 310, a statistics processor 320, and an information providing unit 330.

The diagnosis unit 310 diagnoses a skin condition by comparing and analyzing the received wavelength-specific spectral images with reference values of corresponding wavelength bands for each skin lesion. For example, the diagnosis unit 310 may diagnose the skin condition by comparing and analyzing a skin lesion with a reference value which is stored in advance for each of the wavelengths corresponding to the plurality of optical filters 136 on the basis of each of the plurality of images acquired using the plurality of optical filters 136 of the mobile spectral imaging device 100.

That is, the diagnosis unit 310 may extract a pixel value at a position of the lesion in each of the images, check the reference value that corresponds to the lesion, and generate a spectral spectrum by classifying the extracted pixel value and the reference value by wavelength. In this case, the reference value may correspond to normal skin.

As shown in FIG. 11, the diagnosis unit 310 may generate a spectral spectrum consisting of pixel values of a plurality of images 600 captured in each of the wavelengths corresponding to the plurality of optical filters 136 and reference values that correspond to the pixel values.

It is possible to predict and diagnose various skin diseases including skin cancer, atopic dermatitis, tinea, sailor's skin, and the like by using the spectral spectrum.

Alternatively, the diagnosis unit 310 may compare diseased skin and normal skin on the basis of the generated spectral spectrum and predict and diagnose a pertinent disease.

The diagnosis unit 310 may use a Euclidean distance, a spectral angle mapper, or the like to analyze the spectral image. For example, the diagnosis unit 310 may use a K-means clustering algorithm to automatically analyze data without a reference obtained from a clinical test. In this case, the diagnosis unit 310 may diagnose whether a symptom is a special symptom through a comparison thereof with previously analyzed data.

The statistics processor 320 may quantitatively analyze changes of a specific skin lesion diagnosed by the diagnosis unit 310 and quantitatively analyze a comparison thereof with normal skin. For example, as shown in FIG. 12, the statistics processor 320 may analyze changes over time on the basis of images of a user and a diagnosis result which are transmitted from the user terminal 200, and provide the analysis result. That is, the statistics processor 320 may calculate statistical changes of the lesion over the course of a treatment by using quantitative values or a graph and quantitatively analyze and compare data of the lesion with normal skin as well as the spectrum with a spectrum of normal skin.

The information providing unit 330 may search the server DB 350 for a hospital available for treatment of the skin disease diagnosed by the diagnosis unit 310 and a method of preventing aggravation, and provide the search result to the user terminal 200. For example, the information providing unit 330 may provide relevant information, such as a treatment method for a skin lesion diagnosed as the skin condition, the method of preventing aggravation, or the hospital available for treatment.

The server DB 350 may store a user-specific spectral spectrum generated by the diagnosis unit 310 or reference values used for the spectral spectrum, and disease information for determining a disease of the photographed skin. The server DB 350 may include a user information storage unit 352, an analysis information storage unit 354, and a provision information storage unit 356.

The user information storage unit 352 may store user information that corresponds to the user terminal 200 and an image transmitted from the user terminal 200. That is, the user information storage unit 352 may store the image transmitted from the user terminal 200 and an analysis result of the transmitted image for each user.

The analysis information storage unit 354 may store, for example, a type and characteristic of a skin disease to be analyzed, a type of occurrence, and a reference value of each wavelength band for each skin lesion as information for analyzing the image transmitted from the user terminal 200. In addition, the analysis information storage unit 354 may store symptoms and a spectral spectrum at each stage of each skin disease in order to not only intensively diagnose general skin diseases, such as atopic dermatitis, tinea, acne, scalp, melanoma, and the like, but also to diagnose high-risk skin diseases, such as various skin cancers.

The provision information storage unit 356 may store provision information, such as a treatment method for a skin lesion diagnosed by the diagnosis unit 310, a method of preventing aggravation, or a hospital available for treatment. For example, the information providing unit 330 may store a method of treating the diagnosed skin lesion with a light source of a specific wavelength or a location and contact information of a hospital available for treatment of the pertinent skin lesion.

In one embodiment of the present invention, with the above configuration, it is possible to easily diagnose a skin disease and conveniently and regularly manage skin at home by using a user terminal, such as a smartphone or a tablet computer; it is also possible to provide continuous skin care mentoring through an intensified search function by generating a DB including a variety of information, such as a treatment method and post-treatment care of a skin-related disease, kinds of skin-related diseases, and a treatment method for a current skin condition; and it is possible to diagnose a skin disease, which is increasing due to environmental or genetic factors, at an early stage, thereby alleviating social and economic costs associated with the skin disease.

Figure 13:
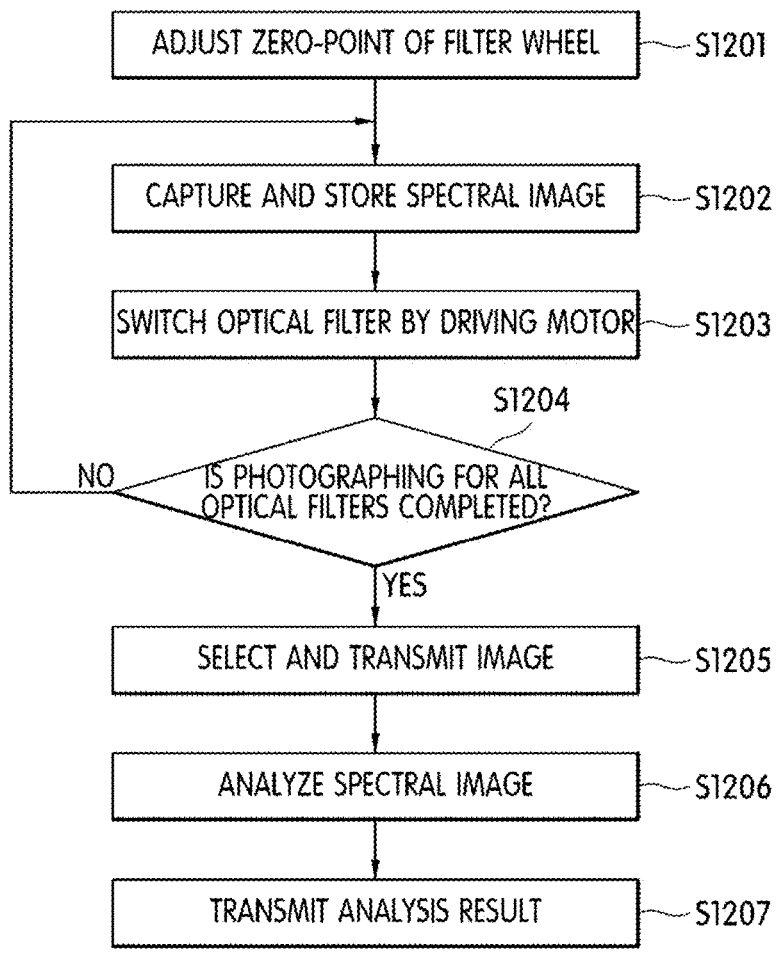
FIG. 13 is a flowchart illustrating a spectral image acquisition and analysis method according to one embodiment of the present invention.

Hereinafter, a spectral image acquisition and analysis method according to one embodiment of the present invention will be described with reference to FIG. 13. FIG. 13 is a flowchart illustrating a spectral image acquisition and analysis method according to one embodiment of the present invention.

A spectral image acquisition and analysis method 1200 includes operations of adjusting a zero-point of the filter wheel 130 (S1201), capturing and storing a spectral image (S1202), switching each of the optical filters 136 according to driving of the driving unit 160 (S1203 and S1204), selecting and transmitting a captured spectral image (S1205), analyzing the transmitted spectral image (S1206), and transmitting an analysis result (S1207).

More specifically, first, after the user terminal 200 equipped with a photographing unit is mounted on the mobile spectral imaging device 100, which is equipped with a plurality of optical filters, a zero-point of the filter wheel 130 in which the plurality of optical filters 136 are formed may be adjusted, as shown in FIG. 13 (operation S1201).

In this case, the mobile spectral imaging device 100 and the user terminal 200 may be paired through a Bluetooth communication, a focal point between a skin to be photographed and the optical system 120 of the mobile spectral imaging device 100 may be adjusted, and an initial photographing position of the filter wheel 130 may be adjusted.

For example, the optical filter 136 having the lowest wavelength band among the plurality of optical filters 136 formed in the filter wheel 130 may be positioned in line with the light source 220. In this case, the horizontal polarimeter 124 may be in line with the optical filter 136 or the magnifying glass 128 may be in line with the vertical polarimeter 126 with respect to the photographing unit 210 or the light source 220 of the user terminal 200.

Then, spectral images of different wavelengths may be captured and stored using one of the plurality of optical filters 136 of the mobile spectral imaging device 100 on which the user terminal 200 having a photographing function is mounted (operation S1202).

In this case, the user terminal 200 may provide a wavelength-specific selection screen for a user to select a specific wavelength for photographing. With this function, when re-photographing is performed for the specific wavelength at a time of continuous photographing using the plurality of optical filters 136, it is possible to capture an image at a selective wavelength.

Then, the optical filter 136 may be switched to photograph a spectral image for a subsequent wavelength band by driving the driving unit 160 (operation S1203).

For example, the filter wheel 130 may be rotated by driving the driving unit 160 such that the optical filter 136 that corresponds to the subsequent wavelength band is positioned in line with the light source 220 of the user terminal 200.

As such, it is possible to capture a spectral image that corresponds to a specific wavelength band while selectively positioning the optical filter which corresponds to a target wavelength band among the plurality of optical filters in an optical path corresponding to the photographing unit.

Then, it is determined whether photographing is completed for all of the optical filters 136 (operation S1204), and when the photographing is not completed for all of the optical filters 136, the operation returns to operation S1202 and operations S1202 to S1203 may be repeatedly performed until the photographing for all of the optical filters 136 is completed.

In this case, the plurality of optical filters 136 may be continuously rotated on the basis of a photographing speed of the photographing unit such that one selected optical filter 136 is placed in the optical path in response to a photographing request of the user terminal 200.

As described above, through operations S1202 to S1204, it is possible to switch the optical filters 136 and complete photographing for all wavelengths by continuously rotating the filter wheel 130 on the basis of the photographing speed of the photographing unit 210 such that each of the plurality of optical filters 136 is positioned in line with the light source 220 of the user terminal 200.

For example, because a spectral image consists of a plurality of wavelength-specific images, target skin is continuously photographed, and in this case, the filter wheel 130 may be rotated continuously according to the continuous photographing speed of the photographing unit 210, such as a camera. That is, it is possible to selectively position the optical filter 136 which corresponds to a target wavelength band in the optical path by rotating the filter wheel 130 in which the plurality of optical filters 136 are spaced apart from each other at regular intervals.

Then, when the user selects an image in a specific wavelength band among spectral images captured at different wavelengths by using the plurality of optical filters 136 and stored in the user terminal 200, the selected image may be transmitted to the spectral image analysis server 300 (operation S1205).

For example, the user terminal 200 may output the acquired image through the display 260 and provide an image selection screen for the user to select an image. In this case, when the user selects all or some of the images, the image transmission module 246 may transmit only the images selected in the display 260 to the spectral image analysis server 300.

Then, the spectral image analysis server 300 may diagnose a skin condition by comparing and analyzing a skin lesion with a reference value which is stored in advance for each of the wavelengths corresponding to the plurality of optical filters on the basis of each of the plurality of images 600 transmitted from the user terminal 200 (operation S1206).

In this case, the spectral image analysis server 300 may generate a spectral spectrum as a result of the analysis. For example, as shown in FIG. 11, a spectral spectrum that represents a pixel value, which corresponds to a lesion, for each of the wavelengths corresponding to the plurality of optical filters 136 and a reference value which is stored in advance for each of the wavelengths may be generated.

More specifically, a pixel value at a position of a lesion in each of the images transmitted from the user terminal 200 may be extracted.

Then, the reference value corresponding to the pertinent lesion may be checked to be compared with the extracted pixel value. In this case, the reference value may correspond to normal skin.

Thereafter, the extracted pixel values and the reference values may be classified by the wavelengths corresponding to the plurality of optical filters 136, that is, the wavelength of the spectral image. In this case, a spectral spectrum may be generated as a result of the classification.

It is possible to predict and diagnose various skin diseases including skin cancer, atopic dermatitis, tinea, sailor's skin, and the like by using the spectral spectrum.

Alternatively, a pertinent disease may be predicted and diagnosed by comparing diseased skin and normal skin on the basis of the generated spectral spectrum.

In this case, a Euclidean distance, a spectral angle mapper, or the like may be used to analyze the spectral image. For example, the spectral image analysis server 300 may automatically analyze data without reference obtained from a clinical test by using a K-means clustering algorithm. In this case, the spectral image analysis server 300 may diagnose whether a symptom is a special symptom through a comparison thereof with previously analyzed data. The analysis result may be stored in the user information storage unit 352 of the server DB 350.

Optionally, the spectral image analysis server 300 may perform statistical processing by quantitatively analyzing changes of a diagnosed specific skin lesion for each user and quantitatively analyzing a comparison thereof with normal skin. That is, the spectral image analysis server 300 may calculate statistical changes of the lesion over the course of a treatment by using quantitative values or a graph and quantitatively analyze and compare data of the lesion with normal skin as well as the spectrum of the lesion with a spectrum of normal skin.

Optionally, the spectral image analysis server 300 may search for a hospital available for treatment of the diagnosed skin disease and a method of preventing aggravation, and provide the search result. For example, according to the diagnosis result, the spectral image analysis server 300 may search the provision information storage unit 356 of the server DB 350 for relevant information, such as a treatment method for the diagnosed skin lesion, the method of preventing aggravation, or the hospital available for treatment, and provide the found information to the user terminal 200.

Then, the spectral image analysis server 300 may transmit the analysis result to the user terminal 200 (operation S1207).

In this case, the transmitted analysis result may include a spectral spectrum that represents a comparison between the captured image and a reference value corresponding to the image such that the user can check a status of the photographed skin.

Alternatively, when the spectral image analysis server 300 predicts and diagnoses a disease of the photographed skin, the spectral image analysis server 300 may transmit the result along with the spectral spectrum to the user terminal 200. In addition, the spectral image analysis server 300 may transmit the user-specific statistical processing and provision information for the pertinent lesion to the user terminal 200 as the result of the analysis.

Although a treatment or prevention method using the mobile spectral imaging device 100 is not described in the present embodiment, the mobile spectral imaging device 100 may include a light source of a specific wavelength for skin treatment or the filter wheel 130 may include the optical filter 136 of the specific wavelength, and in this case, a corresponding skin disease may be treated using the light source or the optical filter.

For example, light emitted from the light source for skin treatment included in the mobile spectral imaging device 100 may be directed toward skin to be treated.

Alternatively, light emitted from the light source 220 of the user terminal 200 may be directed toward the skin to be treated using an optical filter 136 corresponding to a wavelength for treatment, for example, the 630 nm band, among the plurality of optical filters 136.

In one embodiment of the present invention, with the above-described methods, it is possible to easily diagnose a skin disease and conveniently and regularly manage skin at home by using a user terminal, such as a smartphone or a tablet computer; it is also possible to provide continuous skin care mentoring through an intensified search function by generating a DB including a variety of information, such as a treatment method and post-treatment care of a skin-related disease, kinds of skin-related diseases, and a treatment method for a current skin condition; and it is possible to diagnose a skin disease, which is increasing due to environmental or genetic factors, at an early stage, thereby alleviating social and economic costs associated with the skin disease.

The foregoing methods may be implemented by the user terminal and the spectral image analysis server shown in FIG. 1, and, particularly, by software programs that execute the operations, and in this case, such programs may be stored in a computer readable recording medium or transmitted through computer data signals combined with carrier waves over a transmission medium or a communication network.

The computer readable recording medium includes any data storage device that can store data which can be thereafter read by a computer system. Examples of the computer readable recording medium include a read-only memory (ROM), a random-access memory (RAM), a compact disk ROM (CD-ROM), a digital versatile disk ROM (DVD-ROM), DVD-RAM, a magnetic tape, a floppy disk, a hard disk, an optical data storage device, and the like.

Although the preferred embodiments of the present invention have been disclosed for illustrative purposes, those skilled in the art should appreciate that various modifications, additions, and substitutions are possible without departing from the scope and spirit of the invention as disclosed in the accompanying claims.

The invention claimed is:

1. A mobile multispectral imaging device for capturing a wavelength-specific spectral image by using a camera of a user terminal, the mobile multispectral imaging device comprising:

an optical system disposed at a position corresponding to the camera of the user terminal and configured to emit light toward an object to be photographed, collect light reflected from the object to be photographed, and transmit the collected light to the camera; and a filter wheel including a plurality of optical filters spaced apart from each other around an outer circumference thereof and configured to place one of the plurality of optical filters in an optical path according to rotation thereof, wherein each of the optical filters filters the emitted light into a specific wavelength band;

the optical system including a polarimeter in an optical path of the camera;

the polarimeter including at least one of a horizontal polarimeter provided in an optical path of the optical filter and configured to provide the light to the object to be photographed, and a vertical polarimeter configured to collect the light reflected from the object to be photographed and transmit the collected light to the camera;

the horizontal polarimeter and a magnifying glass being disposed in the optical system, and the optical system further including an optical system fixing portion having a groove portion formed below the horizontal polarimeter for inserting the outer circumference of the filter wheel to allow the filter wheel to rotate;

the filter wheel comprising a central wheel shaft to which a motor installed on a main body is connected, and a connection part configured to connect the wheel shaft to a part of an inner diameter of the outer circumference in the shape of a ring of the filter wheel;

the groove portion of the optical system fixing portion being disposed on a lower part of the horizontal polarimeter to enable polarized light to be incident on an optical filter disposed on a lower part of the horizontal polarimeter when the outer circumference of the filter wheel rotates with a part thereof inserted into the groove; and an optical system cover comprising a planoconcave lens disposed on the optical system fixing portion, and disposed on the horizontal polarimeter, wherein the optical system fixing portion further comprises a magnifying glass, the optical system cover further comprises a horizontal polarimeter disposed on the magnifying glass, and light of a terminal of the user is radiated onto skin through the magnifying glass and the horizontal polarimeter.

2. The mobile multispectral imaging device of claim 1, further comprising the motor configured to drive the filter wheel to place one selected filter wheel in the optical path in response to a photographing request of the user terminal.

3. The mobile multispectral imaging device of claim 2, wherein the motor continuously rotates the filter wheel on the basis of a photographing speed of the camera.

4. The mobile multispectral imaging device of claim 1, further comprising a Bluetooth device configured to receive a photographing request or a control command from the user terminal.

5. The mobile multispectral imaging device of claim 1, wherein the optical system further includes a light source configured to emit light toward the object to be photographed.

6. The mobile multispectral imaging device of claim 1, wherein the optical system further includes a light source for skin treatment which treats a skin lesion.

* * * * *